(12) United States Patent
de la Rama et al.

(10) Patent No.: US 10,912,609 B2
(45) Date of Patent: Feb. 9, 2021

(54) PULMONARY VEIN ISOLATION BALLOON CATHETER

(71) Applicant: St. Jude Medical, Cardiology Division, Inc., St. Paul, MN (US)

(72) Inventors: Alan de la Rama, Cerritos, CA (US); Cary Hata, Irvine, CA (US); Tim La, Santa Ana, CA (US); Tho Nguyen, Huntington Beach, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 393 days.

(21) Appl. No.: 15/862,036

(22) Filed: Jan. 4, 2018

(65) Prior Publication Data

US 2018/0193090 A1 Jul. 12, 2018

Related U.S. Application Data

(60) Provisional application No. 62/443,235, filed on Jan. 6, 2017.

(51) Int. Cl.
| | |
|---|---|
| *A61B 18/14* | (2006.01) |
| *A61B 18/12* | (2006.01) |
| *A61B 18/02* | (2006.01) |
| *A61B 18/00* | (2006.01) |
| *A61M 25/01* | (2006.01) |
| *A61B 34/20* | (2016.01) |

(52) U.S. Cl.
CPC .......... *A61B 18/1492* (2013.01); *A61B 18/02* (2013.01); *A61B 18/1206* (2013.01); *A61B 2018/00011* (2013.01); *A61B 2018/0022* (2013.01); *A61B 2018/00375* (2013.01); *A61B 2018/00404* (2013.01); *A61B 2018/00577* (2013.01); *A61B 2018/00613* (2013.01); *A61B 2018/00702* (2013.01); *A61B 2018/00821* (2013.01); *A61B 2018/00839* (2013.01); *A61B 2018/00875* (2013.01); *A61B 2018/0212* (2013.01); *A61B 2018/1407* (2013.01); *A61B 2018/1435* (2013.01); *A61B 2034/2051* (2016.02); *A61M 25/0147* (2013.01)

(58) Field of Classification Search
CPC . A61B 18/02; A61B 18/1206; A61B 18/1492; A61B 2018/00011; A61B 2018/0022; A61B 2018/00375; A61B 2018/00404; A61B 2018/00577; A61B 2018/00613; A61B 2018/00702; A61B 2018/00821; A61B 2018/00839; A61B 2018/00875; A61B 2018/0212; A61B 2018/1407; A61B 2018/1435
See application file for complete search history.

(56) References Cited

U.S. PATENT DOCUMENTS

| | | | |
|---|---|---|---|
| 6,251,109 B1 | 6/2001 | Hassett et al. | |
| 6,645,199 B1 * | 11/2003 | Jenkins | A61B 18/1492 606/41 |
| 6,952,615 B2 | 10/2005 | Satake | |

(Continued)

*Primary Examiner* — Michael F Peffley
(74) *Attorney, Agent, or Firm* — Dykema Gossett PLLC

(57) ABSTRACT

The instant disclosure relates to electrophysiology catheters for tissue ablation within a cardiac muscle. In particular, the instant disclosure relates to an electrophysiology ablation balloon catheter with an electrode coil that is wrapped around at least a portion of the balloon and delivers ablation energy at a desired portion of tissue.

20 Claims, 8 Drawing Sheets

(56) References Cited

U.S. PATENT DOCUMENTS

| | | |
|---|---|---|
| 7,112,198 B2 | 9/2006 | Satake |
| 8,231,617 B2 | 7/2012 | Satake |
| 8,647,339 B2 | 2/2014 | Satake |
| 8,702,619 B2 * | 4/2014 | Wang .................. A61B 5/0215 600/554 |
| 2010/0286684 A1 | 11/2010 | Hata et al. |
| 2011/0301587 A1 * | 12/2011 | Deem ................ A61B 18/1815 606/33 |
| 2012/0143179 A1 * | 6/2012 | Avitall ............... A61B 18/1492 606/33 |
| 2013/0085479 A1 | 4/2013 | de la Rama et al. |

* cited by examiner

PULMONARY VEIN ISOLATION BALLOON CATHETER

CROSS-REFERENCE TO RELATED APPLICATIONS

This application claims the benefit of U.S. Provisional Application No. 62/443,235, filed 6 Jan. 2017, the entire disclosure of which is hereby incorporated by reference as though fully set forth herein.

BACKGROUND a. Field

The instant disclosure relates to catheters, in particular catheters for conducting ablation therapy within a heart or other tissue. In one embodiment, the instant disclosure relates to a catheter for treating cardiac arrhythmias by ablating pulmonary venous tissue or in the vicinity thereto.

b. Background Art

The human heart routinely experiences electrical currents traversing its many surfaces and ventricles, including the endocardial chamber. Just prior to each heart contraction, the heart depolarizes and repolarizes, as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, and death.

Catheters are used in a variety of diagnostic and/or therapeutic medical procedures to correct atrial arrhythmia conditions, including for example, ectopic atrial tachycardia, atrial fibrillation, and atrial flutter.

During atrial fibrillation therapy, a catheter may be manipulated through a patient's vasculature to, for example, a patient's heart, and may carry one or more electrodes which may be used for mapping, ablation, diagnosis, or other treatments. To alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, irreversible electroporation, and high-intensity focused ultrasound.

The foregoing discussion is intended only to illustrate the present field and should not be taken as a disavowal of claim scope.

BRIEF SUMMARY

The instant disclosure relates to electrophysiology catheters for tissue ablation within the heart, or other tissue. In particular, the instant disclosure relates to balloon catheters with flexible electrode coils extending across an outer surface of the balloon and focusing ablative energy at target tissue in contact with the flexible electrode coils.

Aspects of the present disclosure are directed to an ablation balloon catheter apparatus. The ablation balloon catheter apparatus includes a catheter shaft with proximal and distal ends, a balloon, and an electrode coil. The balloon includes proximal and distal ends, the proximal end of the balloon coupled to a distal end of the catheter shaft. The electrode coil extends around at least a portion of the balloon, the electrode coil is configured to transfer energy between the electrode coil and tissue in contact with the electrode coil. In more specific embodiments, the balloon engages a pulmonary vein of a cardiac muscle along a length and circumference of the balloon, thereby placing the electrode coil into contact with the circumferential portion of the pulmonary vein. The electrode coil delivers a tissue ablation therapy to the circumferential portion of the pulmonary vein in contact with the electrode coil.

Some embodiments of the present disclosure are directed to a system for treating atrial fibrillation. The system may include an introducer, a balloon delivery catheter, a balloon, and an electrode coil. The introducer includes a lumen extending through a length of the introducer, and the balloon delivery catheter extends through the lumen of the introducer. The balloon is coupled to a distal end of the balloon delivery catheter. The electrode coil extends around at least a portion of the balloon, engages with a tissue wall of a pulmonary vein, and delivers an ablation therapy along the tissue wall of the pulmonary vein engaged by the electrode coil. In more specific embodiments, the balloon engages with a length and circumference of the pulmonary vein adjacent to the tissue wall engaged with the electrode coil, and insulates the length and circumference of the pulmonary vein engaged by the balloon from the ablation therapy.

Various other embodiments of the present disclosure are directed to a balloon catheter for pulmonary vein isolation. The balloon catheter may include a balloon, a steerable balloon delivery catheter shaft to deploy the balloon into a pulmonary vein, and a tissue ablation means. The balloon is coupled to a distal end of the steerable balloon delivery catheter shaft, deploys from an undeployed configuration, and engages a tissue wall of the pulmonary vein. The tissue ablation means extends around at least a portion of the balloon, and delivers an ablation therapy to the tissue wall of the pulmonary vein in contact with the tissue ablation means. In some more specific embodiments, the tissue ablation means is positioned near a distal portion of the balloon, and engages and conducts an ablation therapy on an ostial circumference of the pulmonary vein. The proximal portion of the balloon insulates a blood pool and the pulmonary vein tissue in contact with a proximal portion of the balloon.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
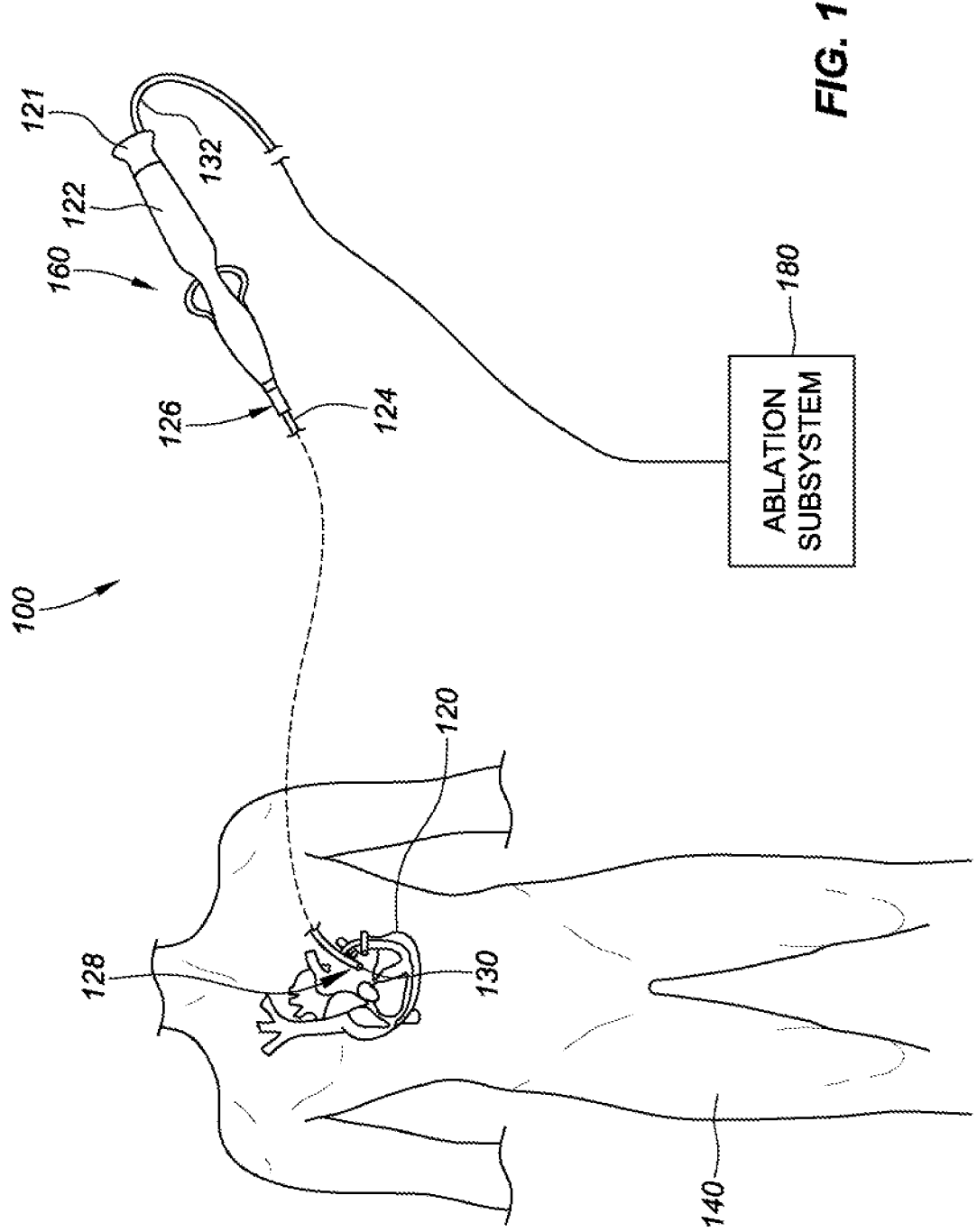
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for tissue ablation within the heart, other organs, and tissue within the body. In particular, the instant disclosure relates to a balloon catheter with flexible electrode coils extending across an outer surface of the balloon for focusing ablative energy at target tissue. In some cardiac-related applications for treating atrial fibrillation, for example, pulmonary venous tissue is ablated to alleviate symptoms and/or cure the condition entirely. Various embodiments of the present disclosure are described below with specific reference to the figures. These embodiments are directed toward atrial fibrillation treatment, but may be readily applied to various conditions, and other organs and tissue within a human body.

Ablation therapies may be delivered by making a number of individual ablations in a controlled fashion in order to form a lesion line. In the case of atrial fibrillation, such lesion lines are often formed around/between the pulmonary veins in the left atrium of the heart, which have been associated with the introduction of erratic electric signals into the heart. Various embodiments of the present disclosure are directed to minimizing applications of energy to the pulmonary veins. Existing designs include ablation balloons with energy applying features within the balloon itself; however, such designs suffer from a lack of ability to focus ablation energy at a target circumference and length of the pulmonary vein during therapy delivery, resulting in energy loss to the blood pool and unintentional ablation of non-target tissue. Moreover, the resulting energy loss may reduce the efficacy of target tissue ablation, cause inconsistent lesion lines, and incomplete electrical signal blockage. In some cases, unintentional ablation of non-target tissue may cause pulmonary vein stenosis, phrenic nerve injury, and esophageal damage.

Radio frequency (RF) point-by-point catheter ablation is one common pulmonary vein isolation technique; however, RF point-by-point catheter ablation is time consuming due to the numerous individual ablations that are required to form the desired linear lesions, and the precise positioning needed. In an effort to simplify and shorten procedure times, circular or loop-type catheters with multiple electrodes for mapping and ablation (e.g., Medtronic's PVAC or Biosense Webster's nMARC) simultaneously conduct each of the individual ablations around a pulmonary vein. Such loop-type catheters mitigate the repetitive positioning concerns of RF point-by-point catheter ablation. However, loop-type catheters often suffer from less than optimal tissue contact. Specifically, the electrodes in the loop-type catheter are not able to conform to a varying geometry of the left atrium and the pulmonary veins (PV). As a result, loop-type catheters often suffer from incomplete electrical signal blockage as one or more of the electrodes lack the necessary tissue contact (during a therapy) to properly ablate the contacted tissue. Aspects of the present disclosure are directed to balloon catheters that facilitate proper electrode-tissue contact by extending a loop-type catheter (also referred to as an electrode coil) into contact with the target tissue (e.g., PV ostia), and creating a contiguous transmural circumferential lesion.

Balloon based ablation has been used for various therapeutic applications in the medical field, including pulmonary vein isolation (PVI) procedures. Embodiments disclosed herein may be readily adapted to utilize various energy sources to deliver the ablation therapy including radiofrequency, ultrasound, laser, cryogenic fluid and others. Aspects of U.S. Pat. Nos. 6,952,615, 7,112,198, 8,231,617, and 8,647,339, disclose various high frequency RF thermal balloon catheters which uniformly ablate the tissue in contact with the balloon, each of which are hereby incorporated by reference as though fully set forth herein. In various embodiments consistent with the present disclosure, lesions may be created through capacitive type heating where transmitted RF energy heats the tissue in contact with the balloon; however, large amounts of energy are lost through non-tissue contacting areas of the balloon, such as portions of the balloon in contact with a blood pool which may act as a highly efficient heat sink. Various embodiments of the present disclosure improve energy delivery efficiency by placing RF electrodes around an outer circumference of a balloon and into direct contact with targeted PV tissue (e.g., antrum and/or ostia). As a result, RF energy is directly delivered to the target pulmonary vein, greatly limiting the energy absorbed by the blood pool or other tissue. In further embodiments, the balloon and/or the fluid inside the balloon may be thermally insulative. As the blood pool is insulated from the RF energy, the incidence for blood coagulation in the stagnant blood pool adjacent the balloon may be greatly reduced. Blood coagulation may be deadly for patients, where the clots are transported through the circulatory system once normal cardiovascular circulation is restored.

Referring now to the drawings wherein like reference numerals are used to identify similar components in the various views, FIG. 1 is a schematic and diagrammatic view of a catheter ablation system 100 for performing a tissue ablation procedure. In one embodiment, tissue 120 comprises cardiac tissue within a human body 140. It should be understood, however, that the system may find applications in connection with a variety of tissue within a human body, and therefore, the present disclosure is not meant to be limited to the use of the system in connection with only cardiac tissue.

Catheter ablation system 100 may include a catheter 160 and an ablation subsystem 180 for controlling an ablation therapy conducted by a balloon 130 at a distal end 128 of the catheter 160. The balloon 130 including a flexible electrode coil extending around an outer surface of the balloon. The ablation subsystem 180 can control the application of, and/or generation of, ablative energy including, for example, radio frequency (RF), cryoablation, laser, irreversible electroporation, chemical, and high-intensity focused ultrasound.

In the example embodiment of FIG. 1, catheter 160 is provided for examination, diagnosis, and/or treatment of internal body tissue such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end of the catheter shaft 124.

In one example embodiment, balloon 130 is manipulated through vasculature of a patient 140 using handle 122 to steer one or more portions of shaft 124, and position the ablation balloon at a desired location within a heart. In various embodiments, ablation elements are distributed across a flexible electrode which extends around the outer surface of the balloon. The ablation elements may be RF coils, IRE ablation electrodes, high intensity focused ultrasound ablation elements, etc. When the ablation elements are operated by ablation subsystem 180, the tissue 120 in contact with the balloon 130 is ablated.

In various specific embodiments of the present disclosure, catheter 160 may include electrophysiology electrodes and one or more positioning sensors (e.g., impedance-based or magnetic positioning sensors) at a distal end 128 of catheter shaft 124. The electrophysiology electrodes acquire electrophysiology data relating to cardiac tissue 120, while the positioning sensor(s) generate positioning data indicative of the three dimensional position of balloon 130. In further embodiments, the catheter 160 may further include other conventional catheter components such as, for example and without limitation, steering wires and actuators, irrigation lumens and ports, pressure sensors, contact sensors, temperature sensors, additional diagnostic electrodes, and corresponding conductors, leads, or traces.

Connector 121 provides mechanical and electrical connection(s) for one or more cables 132 extending, for example, from ablation subsystem 180 to ablation balloon 130 mounted at a distal end 128 of catheter shaft 124. In other embodiments, the connector may also provide mechanical, electrical, and/or fluid connections for cables extending from other components in catheter system 100, such as, for example, a fluid source (when the catheter 160 comprises an irrigated catheter) and contact/pressure sensing circuitry. The connector 121 is conventional in the art and is disposed at a proximal end 126 of the catheter 160.

Handle 122 provides a location for a user to hold catheter 160 and may further provide steering or guidance for the shaft 124 within the body 140. For example, the handle 122 may include means to manipulate one or more steering wires extending through the catheter 160 to a distal end 128 of the shaft 124, thereby facilitating steering of the shaft. The handle 122 is conventional in the art and it will be understood that the construction of the handle may vary. In other embodiments, control of the catheter 160 may be automated by robotically driving or controlling the catheter shaft 124, or driving and controlling the catheter shaft 124 using a magnetic-based guidance system.

Catheter shaft 124 is an elongated, tubular, and flexible member configured for movement within a patient's body 140. The shaft supports a balloon 130 at a distal end 128 of catheter 160. The shaft 124 may also permit transport, delivery and/or removal of fluids (including irrigation fluids, cryogenic ablation fluids, and body fluids), medicines, and/or surgical tools or instruments. The shaft 124, which may be made from conventional materials used for catheters, such as polyurethane, defines one or more lumens configured to house and/or transport electrical conductors, fluids, and/or surgical tools. The catheter may be introduced into a blood vessel or other structure within the body 140 through a conventional introducer.

In one example cardiac ablation therapy, to correct for atrial arrhythmia, the introducer is introduced through a peripheral vein (typically a femoral vein) and advanced into right atrium. In what is referred to as a transeptal approach, an incision in the fossa ovalis is made, and the introducer extends through the incision in the fossa ovalis. The ablation catheter 160 may then be extended through a lumen of the introducer into the left atrium. Catheter shaft 124 of ablation catheter 160 may then be steered or guided through the left atrium to position balloon 130 into a desired location within the left atrium such as a pulmonary vein.

To achieve effective and efficient ablation of target myocardial tissue in contact with balloon 130, one or more electrode coils circumnavigating an outer surface of the balloon 130 are sandwiched between the balloon and tissue. Due to the direct contact between the electrode coils and tissue, energy transfer is focused in a way that limits energy transfer to non-target tissue. Accordingly, aspects of the present disclosure focus energy transfer to target tissue by coupling electrode coils with RF electrodes to an external surface of the balloon where target tissue will interface. As the RF electrodes are in direct thermal contact with the target tissue, and insulated from the non-target tissue and blood pool by the balloon, the RF energy emitted is largely absorbed by the target tissue, thereby increasing the overall efficiency of the system and reducing the risk of unintentional tissue ablation. In various embodiments, the balloon walls, and/or fluid within the walls may have a dielectric effect to further prevent unintentional RF energy distribution. Aspects of the present disclosure are directed to RF energy tissue ablation, and may be readily adapted for direct current electroporation ablation (also referred to as irreversible electroporation (IRE)).

Figure 2:
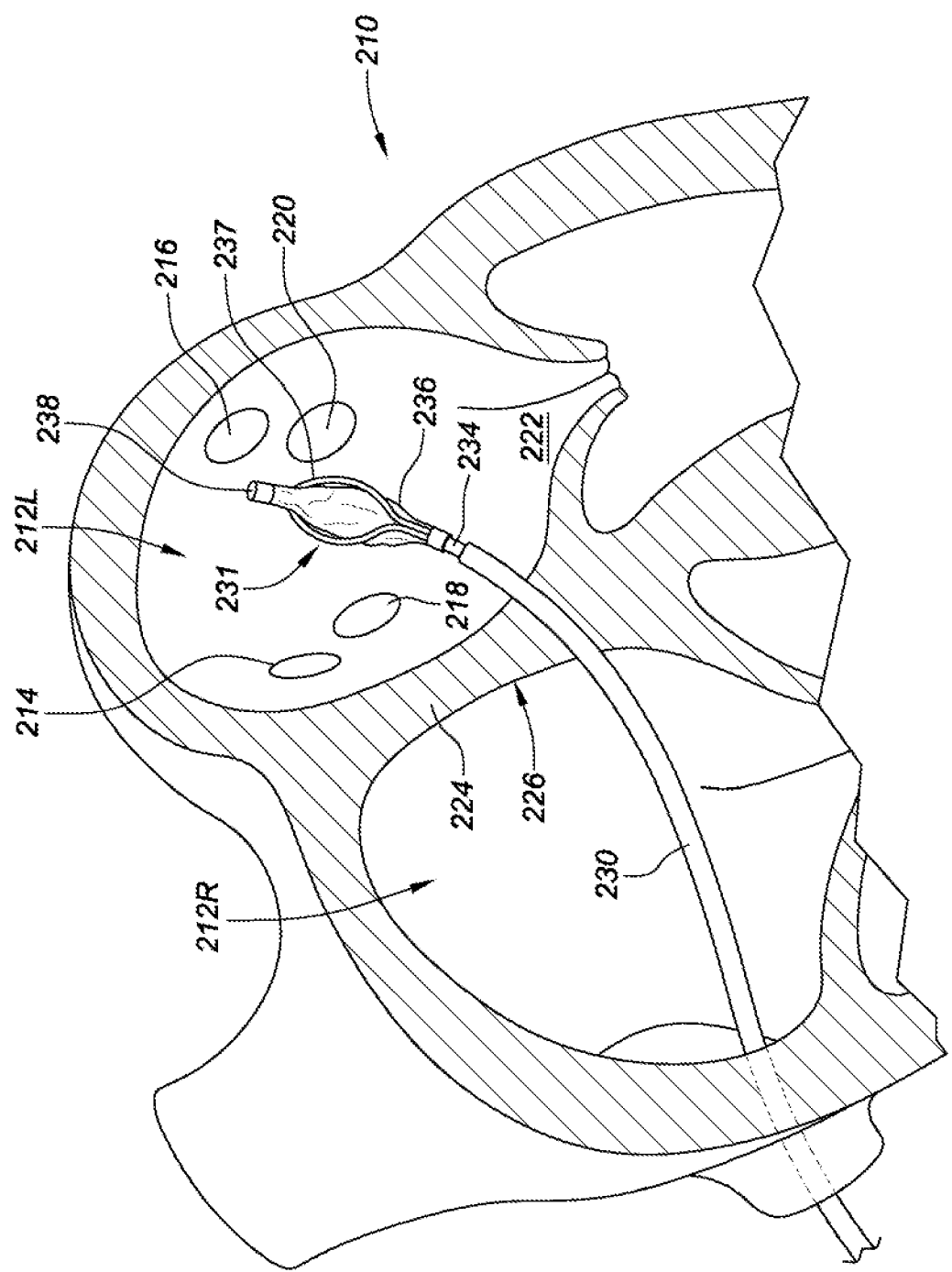
FIG. 2 is a cross-sectional front-view of a left atrium with a collapsed balloon catheter extending out of an introducer and into the left atrium, consistent with various aspects of the present disclosure.

FIG. 2 is a cross-sectional front-view of a portion of cardiac muscle 210 with an balloon catheter 231 locating a pulmonary vein (e.g., 214, 216, 218, and 220) for performing an ablation therapy. As shown in FIG. 2, the cardiac muscle 210 includes two upper chambers called the left atrium 212L and right atrium 212R, and two lower chambers called the left ventricle and right ventricle (partially visible).

Aspects of the present disclosure are directed to ablation therapies in which tissue in pulmonary veins 214, 216, 218, and 220, which form conductive pathways for electrical signals traveling through the tissue, is destroyed in order to electrically isolate sources of unwanted electrical impulses (e.g., arrhythmiatic foci) located in the pulmonary veins. By either destroying arrhythmiatic foci, or electrically isolating the arrhythmiatic foci from the left atrium 212L, the cause of atrial fibrillation symptoms can be reduced or eliminated entirely.

As shown in FIG. 2, an ablation balloon catheter 231 may be introduced into the left atrium 212L by an introducer 230. A distal portion of catheter shaft 234 may guide the ablation balloon 236, once introduced into the left atrium 212L by the introducer 230. Optionally, the ablation balloon catheter 231 may include mapping electrodes at proximal and distal ends of the ablation balloon 236. In operation, introducer 230 has its distal end positioned within left atrium 212L. As shown in FIG. 2, a transeptal approach has been utilized in which introducer 230 is introduced through a peripheral vein (typically a femoral vein), advanced through right atrium 212R into left atrium 212L via a transeptal puncture, and anchored to the wall 226 of the fossa ovalis 224.

Once introducer 230 is in position within left atrium 212L, steerable ablation balloon catheter 231 is advanced out a distal end of the introducer 230 and toward one of the pulmonary veins (e.g., 214, 216, 218, and 220). In FIG. 2, the target pulmonary vein is right superior pulmonary vein 214. A distal portion of the catheter shaft 234 is manipulated until the distal tip of the ablation balloon catheter is directed toward the target pulmonary vein 214.

Where the therapy is directed toward antrum of a pulmonary vein, balloon 236 is deployed, and then extended into contact with the antrum. Alternatively, where the therapy is directed toward a pulmonary vein ostium, the balloon 236 is extended into the pulmonary vein. Carried near a distal end of balloon catheter 231, balloon 236 remains in a collapsed condition so that it may enter into the target pulmonary vein 214. Once in position within the ostium, the balloon 236 is deployed, so that it engages and secures the ablation balloon catheter 231 within the target pulmonary vein 214. In some applications, it may be desirable to occlude the flow of blood from the pulmonary vein into the left atrium. To confirm proper occlusion of the pulmonary vein, fluoroscopic die may be injected into the blood pool within the pulmonary vein (which is visible via fluoroscopic imaging)—where the fluoroscopic die stagnates within the pulmonary vein, the ablation balloon is effectively occluding the pulmonary vein. Once proper position of the ablation balloon is verified, ablation therapy may be initiated.

In FIG. 2, an electrode coil 237 extends around at least a portion of the circumference of balloon 236. When the balloon is radially expanded, the electrode coil 237 is also extended into a deployed configuration about the balloon, and sandwiched between the PV tissue and the balloon 236. The electrode coil 237 includes ablation means, such as RF coils distributed along the coil, and may also include diagnostic/mapping electrodes, and thermocouples.

To ablate tissue, once deployed, the electrode coils 237 may radiate a radiofrequency signal directly into targeted tissue of the pulmonary vein 214. In other embodiments, the electrode coil 237 may conduct a direct current into the target tissue to ablate (commonly referred to as irreversible electroporation). In yet further embodiments, the electrode coil may have one or more expansion chambers distributed about the coil, to which supply and exhaust lumens deliver cryogenic fluid. Upon arrival of cryogenic fluid (cryofluid) at the expansion chambers, the reduction in pressure within the expansion chamber causes a phase change from liquid to gas which absorbs energy from the tissue in contact with the electrode coils 237. In yet other embodiments, the electrode coils 237 may deliver one or more of the following energies to the targeted tissue: laser, chemical, high-intensity focused ultrasound, among others.

Various balloon catheter implementations are envisioned including a balloon for ablating an antrum of a pulmonary vein. In such an embodiment, electrode coil 237 may be positioned toward a distal end of balloon 236. The position of the electrode coil 237 facilitates direct contact between the antrum and the electrode coil 237. Yet other ablation balloon implementations consistent with the present disclosure are directed to ablating a pulmonary vein ostium. In such an embodiment, the electrode coil 237 may encompass a central circumferential portion of the balloon 236. During delivery, the balloon is positioned within a PV so that the electrode coil contacts the ostium when the balloon is expanded, thereby facilitating an ablation therapy of just the ostial tissue. In such an embodiment, tissue and/or the blood pool in contact with the proximal and distal portions of the balloon do not receive ablative energy as the electrode coil 237 is electrically isolated from the ablation therapy by at least the balloon 236.

Figure 3:
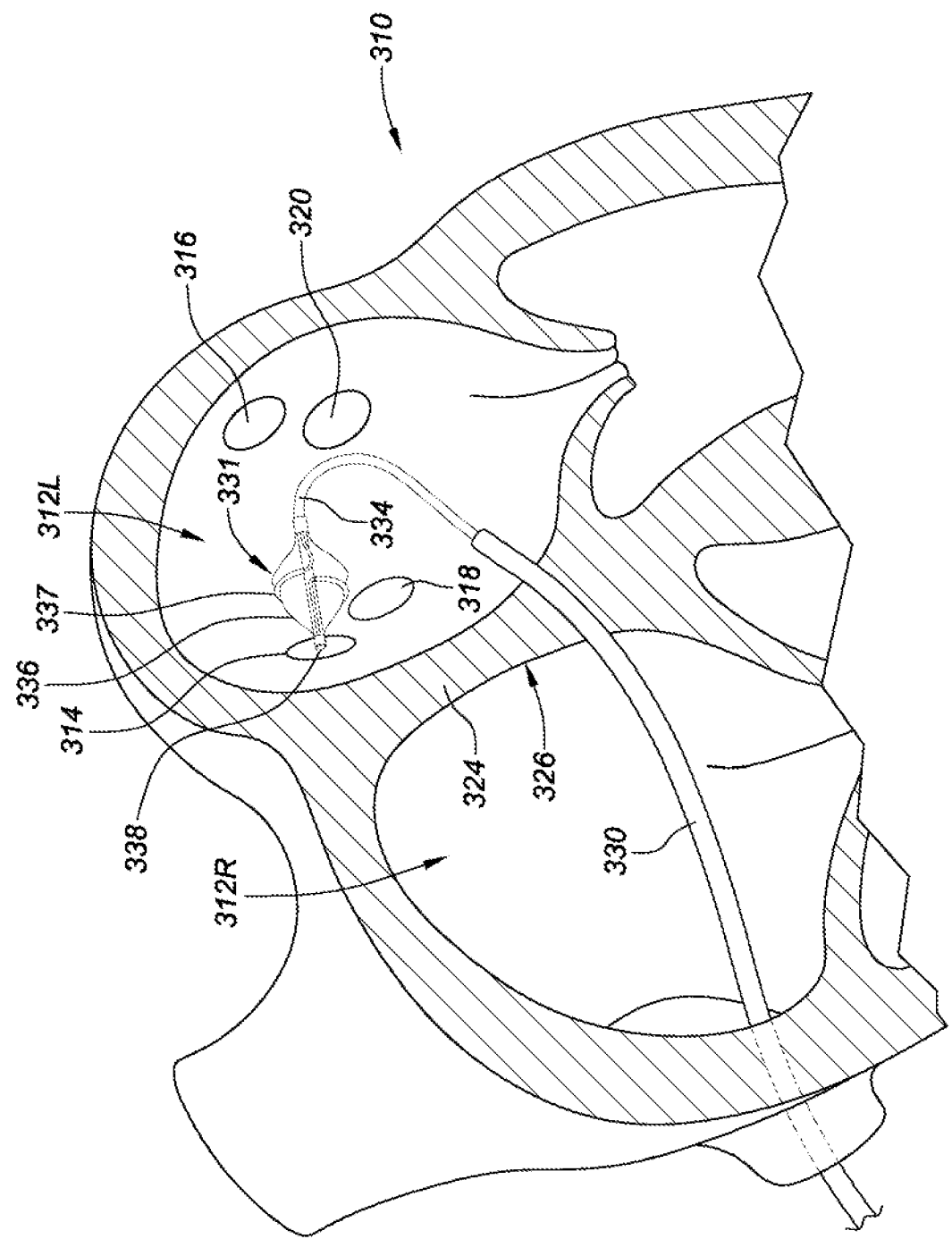
FIG. 3 is a cross-sectional front-view of a left atrium with an expanded balloon catheter locating a pulmonary vein, consistent with various aspects of the present disclosure.

FIG. 3 shows an ablation balloon catheter 331 within a left atrium 312L. The ablation balloon catheter includes a balloon 336 with a circumferentially extending electrode coil 337 advancing through an antral portion of a pulmonary vein 314. As a distal end 338 of the ablation balloon catheter 331 enters the pulmonary vein 314, mapping may be conducted using mapping electrodes attached to the electrode coil 337 and/or attached to the catheter shaft 334 at distal and proximal ends of the balloon 336. The mapping may facilitate proper location of the balloon 336 prior to conducting an ablation therapy.

The electrode coil 337 extends about the balloon 336, and includes an ablation means, such as RF electrodes distributed about the electrode coil. It has been discovered that positioning RF electrodes into direct contact with target tissue for an ablation therapy facilitates precise energy transfer into the target tissue, while minimizing energy transfer to non-target tissue and a blood pool surrounding portions of the balloon. In various embodiments of the present disclosure, the electrode coil 337 may be coupled to an interior or exterior surface of the balloon, integral to the external surface of the balloon (e.g., fused together), or entirely free-standing from the balloon. In yet further more specific embodiments, the electrode coil is free-standing relative to the balloon and may be adjustable via a pull wire or other adjustment mechanism to vary the location of the electrode coil to customize the ablation for a given pulmonary vein topography, or to facilitate multiple ablation locations with a single catheter. Such an embodiment facilitates, for example, subsequent ablation therapies at antral and ostial portions of the pulmonary vein. Moreover, one or more electrode coils may extend around the balloon and take various shapes, as may be desirable for a given application.

After an ablation therapy at a pulmonary vein antrum is complete, for example, the ablation balloon may be collapsed for removal from the cardiac muscle 310 via the introducer 330, or may be repositioned and/or reconfigured to conduct additional ablation therapies to other pulmonary veins and/or to the ostia of target pulmonary vein 314. For example, the electrode coil 337 may be reconfigured relative to the balloon 336 to conduct ablation therapy on the ostia of the target pulmonary vein 314 by moving the electrode coil 337 proximal relative to the balloon 336.

Figure 4:
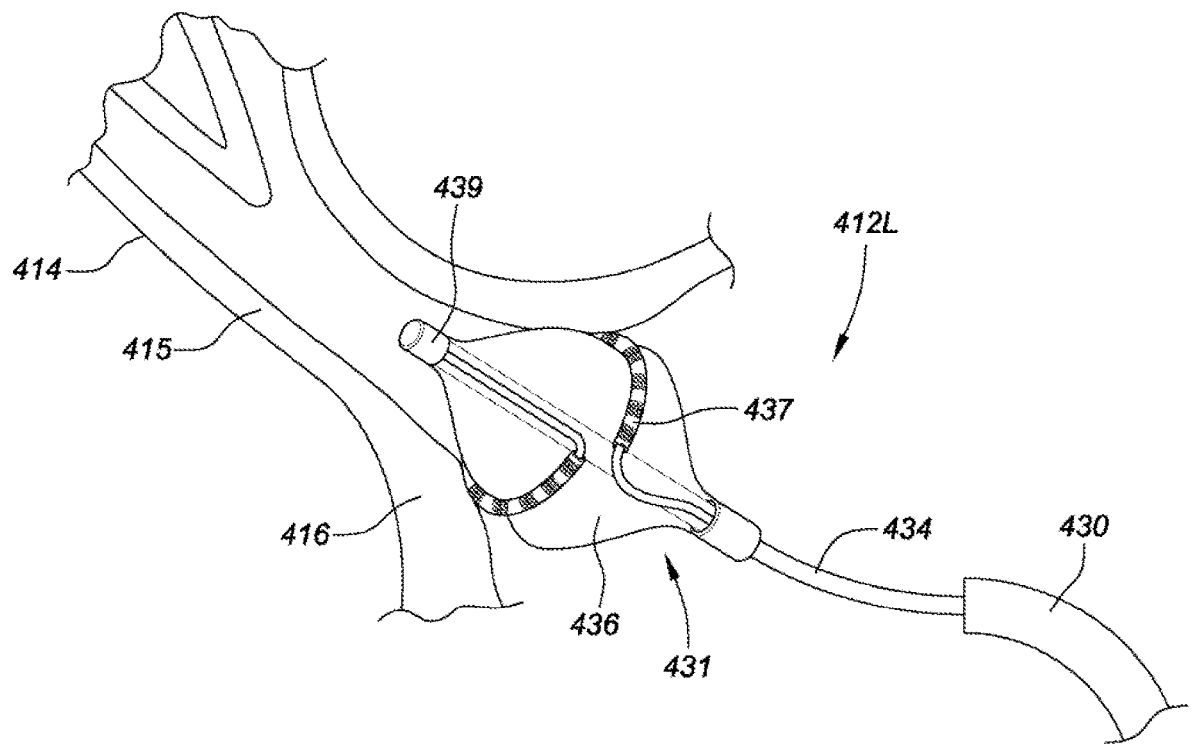
FIG. 4 is a cross-sectional front-view of a pulmonary vein with an expanded balloon catheter positioned in circumferential contact therewith, consistent with various aspects of the present disclosure.

FIG. 4 shows an ablation balloon catheter 431 with a balloon 436 positioned in contact with an antral portion 416 of pulmonary vein 414. An electrode coil 437 circumferentially extends about the balloon 436, and is positioned between the balloon 436 and the antrum 416. In the present embodiment, the ablation balloon catheter 431 is positioned to conduct an ablation therapy of the antrum 416 of the target pulmonary vein 414. The ablation therapy ablates a circumferential ring around the antrum 416 using RF electrodes distributed about the electrode coil 437. By directly contacting the target tissue with the RF electrodes, a larger percentage of power emitted by the RF coil may be received by the target tissue—thereby limiting the flow of RF energy to non-target tissue and the blood pool. The circumferential zone of ablation electrically isolates the left atrium 412L from electrical impulses produced by arrhythmiatic foci opposite the ablation.

As shown in FIG. 4, prior to inflation of ablation balloon 436, introducer sheath 430 delivers the ablation balloon catheter 431 into left atrium 412L. Catheter shaft 434 further aligns the balloon with target pulmonary vein 414. While therapy of antrum 416 may include expanding the balloon 436 before contacting the target tissue, therapy of pulmonary vein ostia 415 may require that distal tip 439 of the balloon catheter 431 be inserted into the pulmonary vein 414 before inflation.

In various embodiments of the present disclosure, ablation balloon catheter 431, due at least in part to the direct contact between electrode coil 437 and target tissue 416, facilitates efficient energy transfer between the RF coils within the electrode coil 437 and the target tissue. Due to the close correlation between the power delivered to the RF coil by a signal generator and the actual power absorbed by the target tissue, estimating an area of the resulting lesion at each of the RF coils based on the power delivered may be achieved. Due to the reliable estimation of lesion size, ablation therapy efficacy may be greatly improved, while reducing the likelihood that a follow-up ablation therapy and/or the use of a single-point ablation catheter for touch-up will be necessary.

In a typical ablation therapy, all pulmonary veins are treated. The processes as described herein for right superior pulmonary vein 214 may be replicated for each of the three other pulmonary veins, as shown in FIGS. 2-3.

Figure 5:
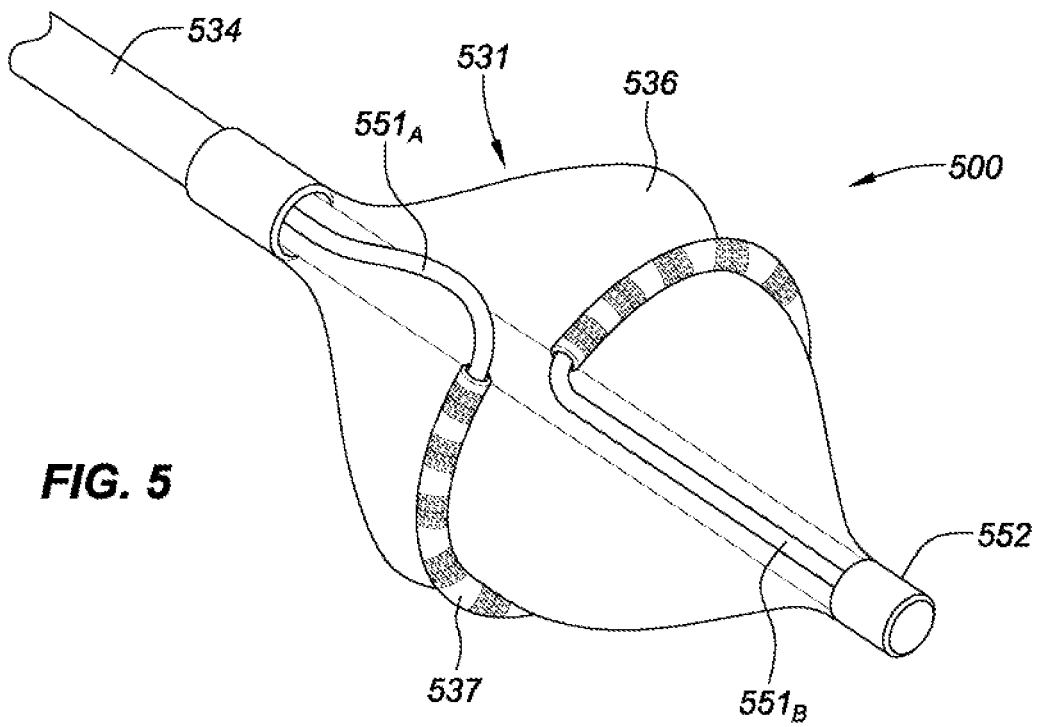
FIG. 5 is an isometric side view of a deployed balloon catheter, consistent with various aspects of the present disclosure.

FIG. 5 shows an isometric view of an ablation balloon catheter 500 with a distal portion 552 including an expanded balloon 536 and an electrode coil 537 circumferentially extending around the balloon. The electrode coil is coupled to the catheter shaft 534 at locations distal 552 and proximal the balloon 536 via lead wires 551A-B. Alternatively, the electrode coil 537 may be coupled to the catheter shaft 534 by external support structures with lead wires extending within a lumen or along an exterior surface, or via flexible electrical circuits that are electrically coupled to the electrode coil 537 and to ablation controller circuitry at a proximal end of the catheter shaft 534. The expanded balloon 536 facilitates contouring of the electrode coil 537 to a length and circumference of a pulmonary vein. The electrode coil 537 may include one or more RF emitters (e.g., an RF coil) distributed about the electrode coil 537, which in response to a driving signal radiates RF energy into tissue in contact with the electrode coil, thereby ablating the tissue. The electrode coil 537 may be fitted into a concave feature within an exterior surface of the balloon 536, facilitating constant contact between the balloon 536 and electrode coil 537 with a length and circumference of a pulmonary vein. While the direct contact between the electrode coil and tissue helps to facilitate efficient heat transfer to the tissue, the concave feature of the balloon 536 about the electrode coil 537 insulates non-target tissue of the pulmonary vein from the emitted RF energy. In some embodiments, it may be desirable for the balloon material and/or fluid within the balloon to be electrically insulative. Such an ablation balloon reduces ablation therapy times due to the improved energy delivery to the target tissue, or may produce enhanced zones of ablation while maintaining therapy times.

Once ablation therapy is complete, balloon 536 may be collapsed, which will simultaneously collapse electrode coil 537, and ablation balloon catheter 534 may be retracted back into introducer 330 (see, e.g., FIG. 3). An electrophysiology catheter, or electrodes proximal and distal to the ablation balloon 536 (for example), may be used to verify the efficacy of the therapy prior to removal of the ablation balloon catheter 531.

In various embodiments of the present disclosure, electrode coil 537 may also include diagnostic and/or mapping electrodes. These electrodes may be used before, during, and after the ablation therapy. For example, prior to the ablation therapy, the diagnostic electrodes may be used to determine optimal positioning of the balloon to increase electrical isolation of the target pulmonary vein from the left atrium. During the ablation therapy, the diagnostic electrodes may be used to track the ablation efficacy. Specifically, the sensed data from the diagnostic electrodes may be used to determine when sufficient isolation between the pulmonary vein and the left atrium has been accomplished. Similarly, after completion of an ablation therapy, the diagnostic electrodes may be used to determine the efficacy of the ablation therapy (including, e.g., ablation lesion characteristics such as depth and surface area, as well as resistance to electrical stimulus), and whether additional therapy applications may be required.

Medical-device type balloons have been developed for a variety of different applications and take a number of different forms. Aspects of the present disclosure may utilize balloons of various types and mechanical construction. The balloons may be either self-erecting (e.g., structurally biased toward a deployed configuration) or mechanically erected (e.g., via pull wire, or introduction of a fluid within the balloon). In one example embodiment, a lumen extending through a length of a shaft 534 of the ablation balloon catheter 500 may inject a fluid into the ablation balloon which exerts a radial force on the ablation balloon—thereby expanding the balloon into a deployed configuration. While various embodiments of the present disclosure have been directed to the treatment of atrial fibrillation within pulmonary veins of a human heart, aspects of the present disclosure are not to be construed so narrowly, but may instead be applied to various types of tissue, and organs within a human body.

Figure 6:
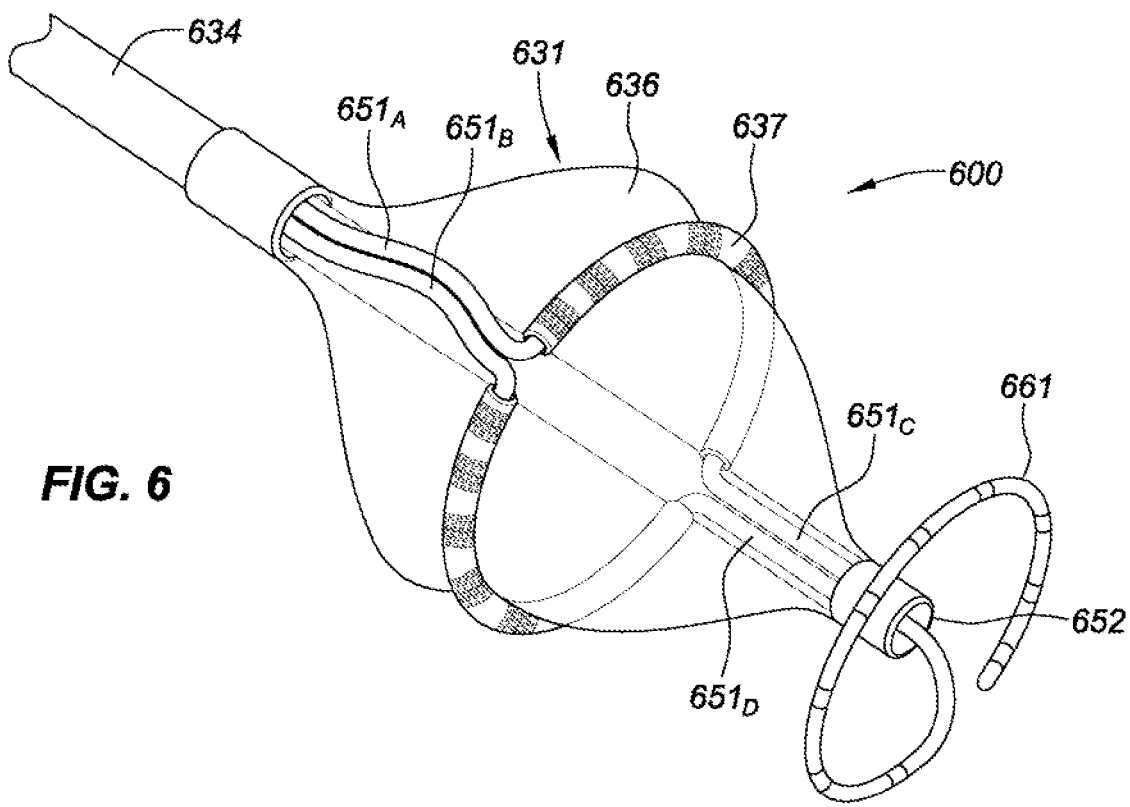
FIG. 6 is an isometric side view of a deployed balloon catheter and an electrophysiology loop catheter extending through a central lumen of the balloon catheter, consistent with various aspects of the present disclosure.

FIG. 6 is an isometric side view of a deployed ablation balloon catheter system 600 with an ablation balloon catheter 631 and an electrophysiology loop catheter 661 extending through a distal end of a central lumen 652 of the ablation balloon catheter, consistent with various aspects of the present disclosure. Balloon 636 is coupled to a distal end of a catheter shaft 634 of the ablation balloon catheter 631. The central lumen 652 extends from a proximal to a distal end of catheter shaft 634, and facilitates the use of electrophysiological electrodes on the electrophysiology loop catheter 661 to retrieve electrophysiological data related to tissue distal the balloon 636. In some applications, electrophysiology catheters may be positioned on either side of the balloon 636 and facilitate collection of electrophysiological characteristics of the pulmonary vein to establish information including the efficacy of an ablation therapy. In one specific embodiment, the electrophysiology loop catheter 661 may be used as a reference while diagnostic electrodes on the electrode coil 637 provide data indicative of the electrical signals received by the left atrium of the heart, for example. Such a configuration is particularly useful after an ablation therapy to determine the efficacy of the lesion to block electrical signals from the pulmonary vein.

As shown in FIG. 6, two half-circle electrode coils 637 circumferentially extend about an outer diameter of balloon 636. The electrode coils 637 are positioned longitudinally along the balloon 636, where the balloon is to contact target tissue for an ablation therapy (e.g., a pulmonary vein ostia or antrum). The electrode coils 637 may be mechanically coupled to the balloon 636 or freely floats above a surface of the balloon and maintained at a relative longitudinal dimension by lead wires 651A-D (or alternatively, flexible electrical circuits). The lead wires 651A-D electrically couple the RF electrodes, and any additional electronic hardware on or within the electrode coils 637 (e.g., diagnostic electrodes, thermocouples, pressure sensors, 3-D mapping electrodes, etc.), to control circuitry at a proximal end of the ablation catheter 631. In the present embodiment, lead wires 651A-B extend distally along a surface of the balloon 636 from a proximal end of the balloon to the electrode coils 637, while lead wires 651C-D extend distally from the electrode coils 637 to a distal end of the balloon 636. In various embodiments, it may be desirable for the lead wires to exhibit some stiffness to maintain a longitudinal position of the electrode coils 637 while the balloon 636 maintains the circumferential profile of the electrode coils. When RF electrodes distributed along the electrode coils 637 are operated, the tissue in contact with the RF electrodes are ablated to create lesions which resist the conductive transfer of electrical signals between the pulmonary vein and the left atrium. As the electrode coils 637 almost completely circumnavigate the balloon 636, with the appropriate combination of RF electrode distribution, and ablation therapy time and power, the ablation lesion may essentially form a contiguous, transmural, circumferential lesion. Where the ablation lesion gap at the juncture between the electrode coils 637 facilitates excessive electrical signal injection into the left atrium, RF coils adjacent the juncture may be driven with more power than the interior RF coils to increase the ablation lesion area near the juncture, thereby bridging any lesion gap. In other embodiments, the electrode coils 637 may circumferentially extend around the balloon 636 at least one complete rotation.

In acute atrial fibrillation cases, it may be desirable to greatly increase the amount of lesioned tissue in a pulmonary vein to maximize the electrical insulation between the pulmonary vein and the heart. In such embodiments, the ablation balloon catheter 631 may include multiple, longitudinally offset electrode coils 637 that form complimentary circumferentially extending lesions in the pulmonary vein. These lesions, in conjunction with the healthy tissue between the lesion rings, greatly reduce the symptoms of, or cure all together, a patient's atrial fibrillation. The redundancy of two or more distally offset, circumferential lesions in the pulmonary vein help to mitigate the occurrence of ineffective ablation therapy. Reasons that an ablation balloon catheter may fail to create a contiguous transmural circumferential lesion include insufficient pressure, lack of contact altogether due to irregular pulmonary vein topography, and inflexibility of the ablation balloon catheter 631. Spiraling electrode coil configurations may also provide enhanced electrical isolation between the pulmonary vein and left atrium. While a spiraling lesion may still allow an undisturbed, electrically conductive path between the pulmonary vein and left atrium, that path is considerably extended. As a result, most electrical signal traffic to the heart will be isolated, and the signal that does successfully traverse through the spiraled lesion will have a reduced signal strength due to the imperfect conductivity of the PV tissue.

To facilitate transport of a balloon 636 of an ablation balloon catheter 631 through an introducer and into position with a pulmonary vein, the balloon 636 is transported in a collapsed configuration. Prior to an ablation therapy, the balloon 636 may be inflated using a fluid that is delivered to the balloon 636 via a lumen extending a length of catheter shaft 634. The introduction of the fluid within the balloon 636 exerts a radial force that inflates the balloon 631. The radial force of the expanding balloon 636 extends an electrode coil 637 encompassing the balloon 631 to a deployed configuration. When positioned in contact with a pulmonary vein ostia, for example, the radial force exerted upon the electrode coil 637 by the balloon 636 facilitates consistent electrode-tissue contact. When an ablation therapy is complete, the balloon 636 may be deflated by drawing fluid out of the balloon 636. In yet other embodiments, the balloon 636 and/or the electrode coil 637 may include a biased/deformable structure that may be deformed for delivery and removal of the ablation balloon catheter 631 via an introducer. The structural bias of the balloon 636 and/or the electrode coil 637 further facilitating expansion of the balloon 636 upon exiting the introducer and/or upon activation of a control wire. Such an embodiment may reduce the complexity of the ablation balloon catheter system 600 by eliminating the need for fluid flow through lumens within the catheter shaft to enact inflation and deflation of the balloon 636.

Figure 7:
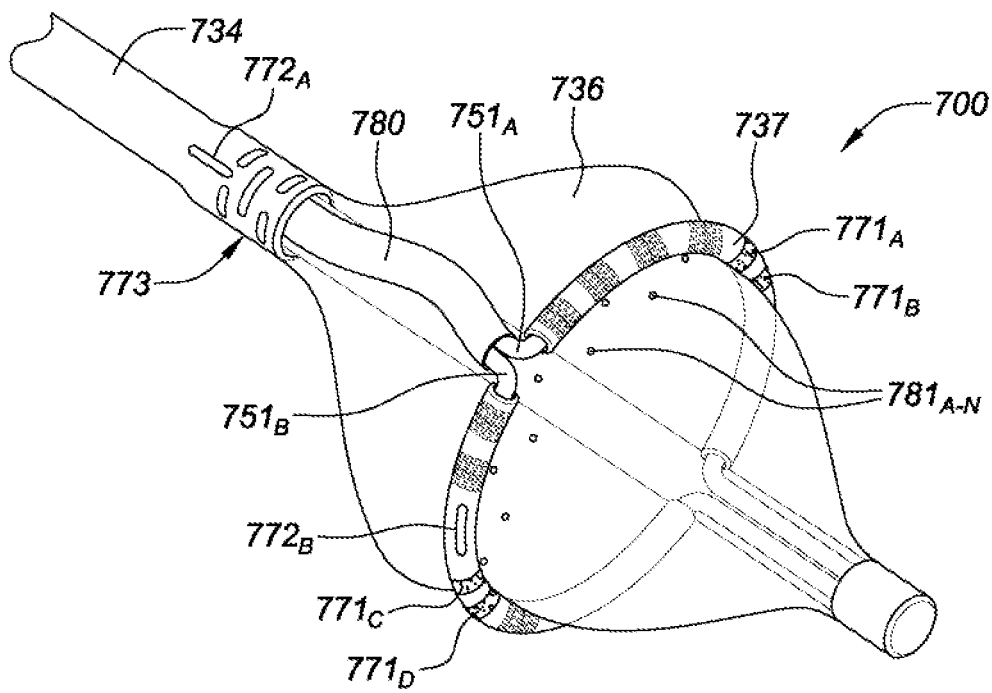
FIG. 7 is an isometric side view of a deployed balloon catheter, consistent with various aspects of the present disclosure.

FIG. 7 is an isometric side view of a deployed balloon catheter 700 with two electrode coils 737. Each of the electrode coils 737 extend approximately half way around a circumference of balloon 736. The electrode coils 737 are coupled at proximal and distal ends of the balloon 736 via lead wires $751_{A-B}$. To help prevent electrode coil spread (which may prevent the electrode coils fitting snugly around the balloon 736 when deployed), an anchor tube 780 may extend over a portion of both lead wires $751_{A-B}$. Distal lead wires may similarly utilize an anchor tube to prevent electrode coil spread. In various embodiments of the present disclosure, the electrode coils 737 may include not only electrodes for ablating tissue in contact with the electrode coils, but may also include multi-mapping electrode(s) $771_{A-D}$ (for conducting electrophysiology mapping, for example), and magnetic sensor(s) $772_B$ (for localization of the balloon 736). The electrode coil 737 may include one or more of each of the multi-mapping electrodes $771_{A-D}$ and the magnetic sensor $772_B$.

During an ablation therapy, electrodes within the electrode coils 737 transfer energy between the electrode coils 737 and tissue in contact therewith. The ablation therapy may also inadvertently transfer some energy to the blood pool surrounding the electrode coils 737, which may cause blood coagulation on and around the electrode coils, as well as blood charring on the electrode coils themselves. To minimize blood coagulation and charring, the fluid used to inflate balloon 736 may be irrigant fluid, and is evacuated from the balloon via irrigant ports $781_{A-N}$ that extend around a circumference of the balloon in proximity to the electrode coils 737. The flow of irrigant fluid in proximity to the electrode coils 737, during an ablation therapy, mitigates blood coagulation and charring on and around the electrode coils.

To further facilitate localization of a balloon catheter 700, a distal portion of catheter shaft 734 may include a magnetic sensor $772_A$, which may be utilized in conjunction with magnetic sensor $772_B$, to facilitate precise localization of the balloon catheter 700. By utilizing both of the magnetic sensors $772_{A-B}$, orientation of the balloon catheter may also be determined. In yet further embodiments, a distal portion of catheter shaft 734 may also include a contact force sensor assembly 773 which may determine a force exerted between balloon 736/electrode coils 737 and tissue (e.g., an antral portion of a pulmonary vein). In some specific embodiments, the contact force sensor assembly 773 may not only determine a force but also a vector of the force exerted on the balloon. Accordingly, a clinician may be able to determine when the electrode coils 737 are making consistent contact with a circumferential portion of a pulmonary vein, for example. In some applications, a force vector exerted along a longitudinal axis of the balloon catheter 700 may be indicative of consistent circumferential contact, whereas an off-axis force vector may be indicative of inconsistent contact with the pulmonary vein and therefore may result in an inconsistent ablation lesion. An inconsistent ablation lesion may negatively impact the efficacy of the ablation therapy.

Figure 8A:
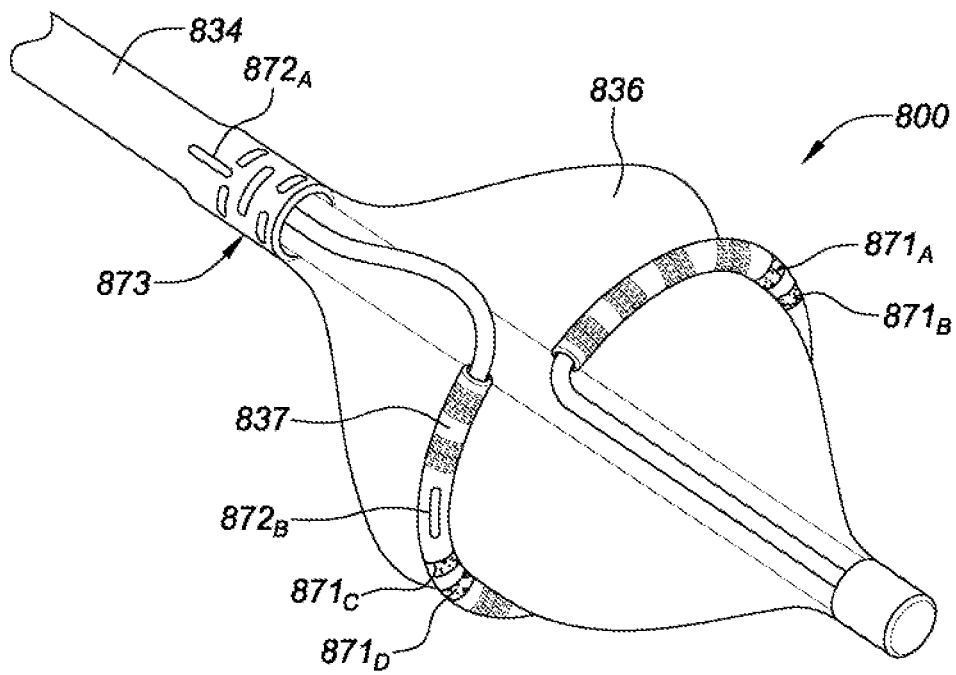
FIG. 8A is an isometric side view of a deployed balloon catheter, consistent with various aspects of the present disclosure.

FIG. 8A is an isometric side view of a deployed balloon catheter 800 including a single electrode coil 837 that helically wraps around a circumferential portion of balloon 836. The electrode coil 837 may include one or more multi-mapping electrodes $871_{A-D}$ and magnetic sensors $872_B$ distributed along a length of the electrode coil. To further facilitate localization of a balloon catheter 800, a distal portion of catheter shaft 834 may include a magnetic sensor $872_A$, which may be utilized in conjunction with magnetic sensor $872_B$ to facilitate precise localization of the balloon catheter 700. By utilizing both of the magnetic sensors $872_{A-B}$, orientation data of the balloon catheter may also be determined. In yet further embodiments, a distal portion of catheter shaft 834 may also include a contact force sensor assembly 873 which may determine a force exerted between balloon 836/electrode coil 837 and tissue.

Figure 8B:
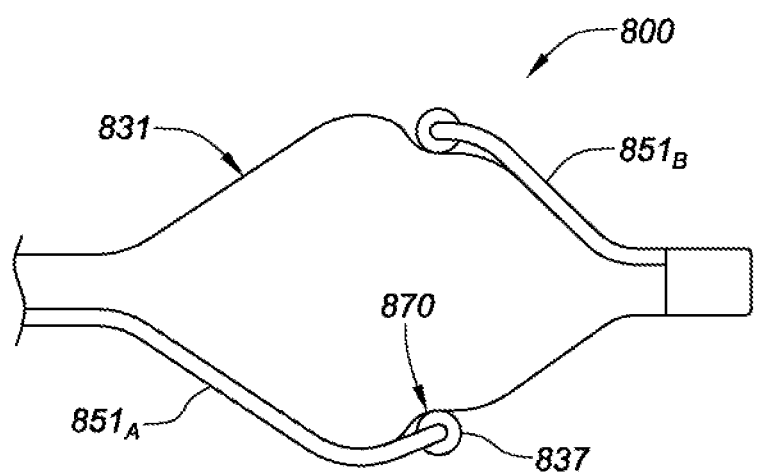
FIG. 8B is a profile view of the deployed balloon catheter in FIG. 8A, consistent with various aspects of the present disclosure.

FIG. 8B is a profile view of a portion of a balloon catheter 800 including a balloon 831 with an electrode coil 837 extending circumferentially around the balloon. As shown in FIG. 8B, the electrode coil 837 is electrically coupled to lead wires $851_{A-B}$ (one extending distally and the other proximally relative to the electrode coils). The lead wires $851_{A-B}$ may also structurally support the electrode coil 837 and facilitate longitudinal positioning of the electrode coil relative to balloon 831. Alternatively, the electrode coil 837 may be coupled to the catheter shaft by external support structures with lead wires extending within a lumen or along an exterior surface, or via flexible electrical circuits that are electrically coupled to the electrode coil 837 and to ablation controller circuitry at a proximal end of the catheter shaft. The expanded balloon 831 facilitates contouring of the electrode coil 837 to a length and circumference of a pulmonary vein. The electrode coil 837 may include one or more RF emitters (e.g., an RF coil) distributed about the electrode coil 837, which in response to a driving signal radiates RF energy into tissue in contact with the electrode coil, thereby ablating the tissue. As shown in FIG. 8A, the electrode coil 837 is fitted into a concave feature 870 within an exterior surface of the balloon 831, facilitating constant contact between the balloon 831/electrode coil 837 with a length and circumference of a pulmonary vein, for example.

Figure 8C:
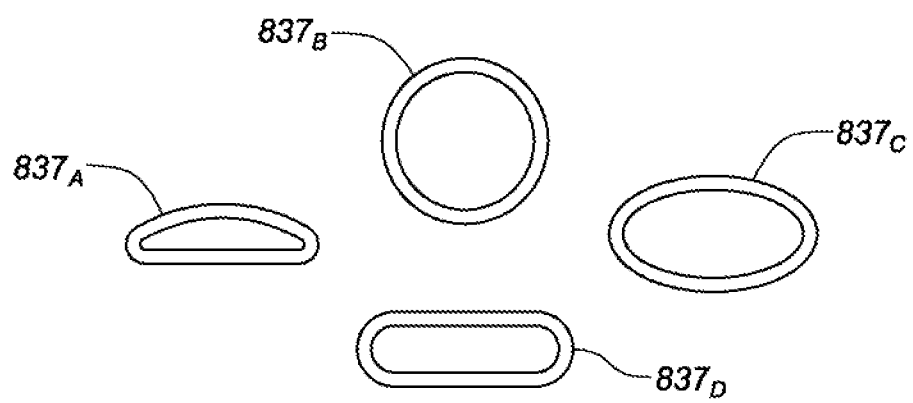
FIG. 8C is a cross-sectional side view of various electrode coil profiles, consistent with various aspects of the present disclosure.

FIG. 8C is a cross-sectional side view of various electrode coil profiles $837_{A-D}$, consistent with various aspects of the present disclosure. Electrode coil profile $837_A$ is a semi-circle, electrode coil profile $837_B$ is circular, electrode coil profile $837_C$ is oval, and electrode coil profile $837_D$ is generally rectangular with rounded corners. Various other electrode coil profiles are readily envisioned.

Figure 9:
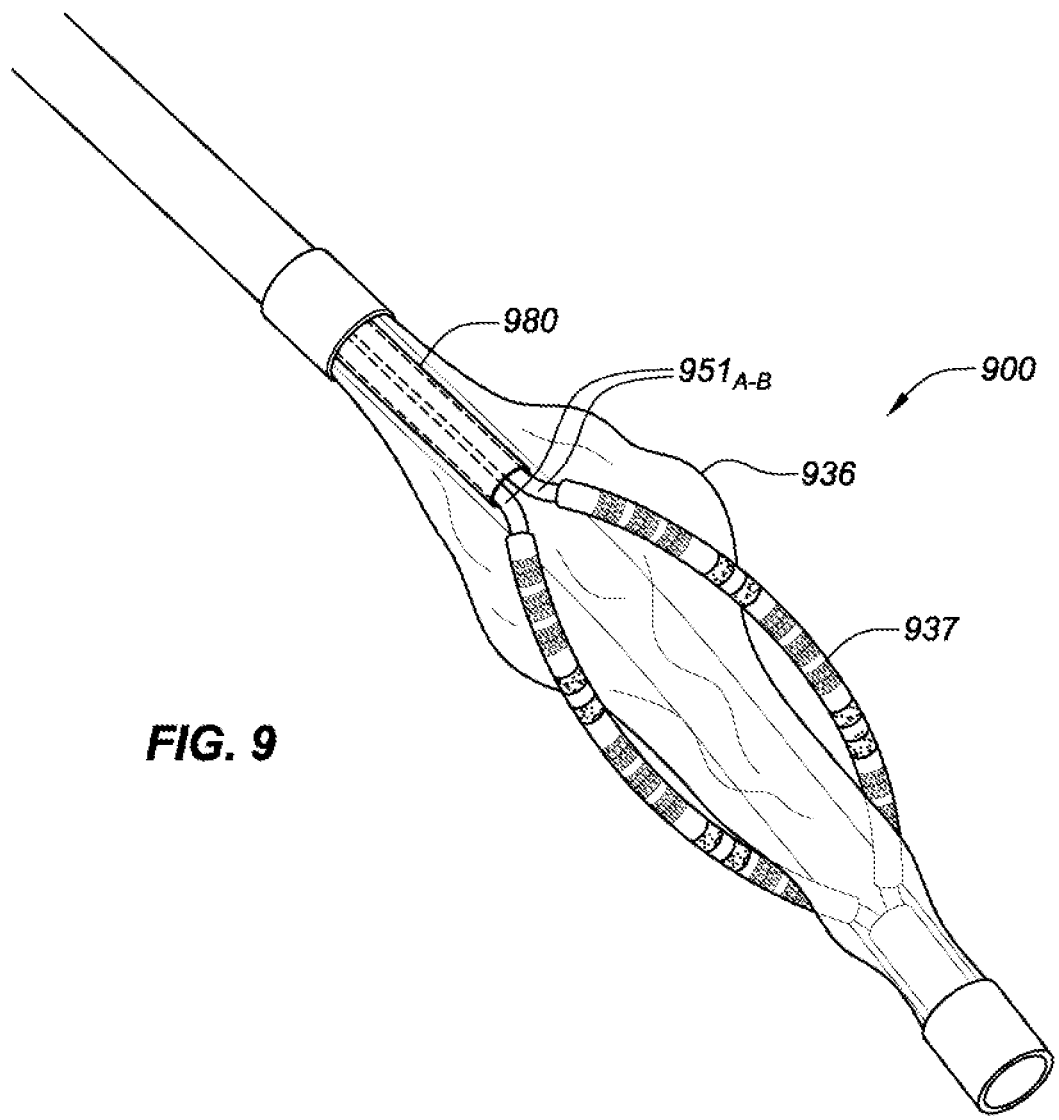
FIG. 9 is a profile view of an undeployed balloon catheter, consistent with various aspects of the present disclosure.

FIG. 9 is a profile view of an un-deployed balloon catheter 900, consistent with various aspects of the present disclosure. In FIG. 9, balloon 936 is un-deployed, facilitating electrode coils 937 to collapse to a rest state (e.g., utilizing shape-memory materials). In some embodiments, guidewires may extend through at least a portion of anchor tube 980 and/or lead wires $951_{A-B}$ to facilitate collapsing the electrode coils 937. The deploying of the balloon 936 radially expands the electrode coils 937 about a circumference of the balloon.

Various balloon catheters consistent with the present disclosure include an electrode coil surrounding a balloon at the distal end of the catheter. The electrode coil may be integrated with the balloon itself, or independent therefrom. In some embodiments, the balloon and the electrode coil may be deployed (after delivery to a target tissue site) by introducing a fluid into a chamber within the balloon. In other embodiments (or in conjunction with the previous embodiment), the electrode coil may be integral to the balloon and have a structural bias that assists expansion of the balloon upon exiting an introducer, for example. When the balloon is expanded into contact with tissue, the RF electrodes, temperature sensors, and diagnostic mapping electrodes on the electrode coil are sandwiched between the balloon and the tissue. Electrical traces or lead wires extending from the RF electrodes, temperature sensors, and diagnostic mapping electrodes may be integrated within the electrode coil (or an external support structure that mechanically supports the electrodes and sensors), or may extend along one or more surfaces of the electrode coil and/or external support structure, and then through a lumen within a catheter shaft to a handle. Various embodiments may utilize flexible circuitry to electrically couple the electrodes to lead wires within the catheter shaft and to facilitate the inflation and deflation of the balloon.

In electrode coil embodiments utilizing flex circuitry, the flex circuitry may include RF electrodes, diagnostic electrodes, and thermocouples that are electrically coupled to controller circuitry (e.g., an ablation subsystem, and an electrophysiology mapping system). The flexible electronic circuit may be mounted directly to the balloon, or to an external structure that at least partially encompasses the balloon. In other embodiments, the flex circuit may extend through a length of the catheter shaft, eliminating the need for a junction between the flex circuit and lead wires within the catheter shaft.

Diagnostic electrodes on the electrode coils (and/or on the external structure that includes the electrode coils) may be utilized to measure electrical potentials across ablated tissue. Where the electrode coils include temperature sensors, the sensed temperature at the electrode-tissue interface may be used to monitor tissue heating and to control ablation therapy power. By focusing generated energy on targeted tissue and limiting the transfer of energy to the blood pool and non-target tissue by positioning the electrode coils in contact with target issue, power required for ablation may be greatly reduced.

Flexible electrode coils, as disclosed in the various embodiments of the present disclosure, may conform to various shapes. To allow for such flexibility, the electrode coils may be laser cut (or otherwise formed, modified, and/or machined) to control the shape of the electrode coil when the balloon is inflated (e.g., the electrode coil is placed under stress). Upon deflation of the balloon, the electrode coil may return to a biased shape/size (e.g., FIG. 9). In such embodiments, once returned to a biased shape/size, the balloon catheter may be withdrawn through the introducer. Various flexible electrode coils are disclosed in U.S. Patent publication 2010/0286684, which is hereby incorporated by reference as though fully set forth herein. Structures for various multiple flexible electrodes are further disclosed in U.S. Patent publication 2013/0085479, which is hereby incorporated by reference as though fully set forth herein. For example, the embodiment disclosed in FIG. 5 of U.S. Patent publication 2013/0085479 may be readily adapted in view of the present disclosure. Such a combination may further utilize one or more additional electrodes for mapping and pacing between RF ablating electrodes. Extended irrigation lumen(s) with variable holes to facilitate delivery of fluid equally along the length of the ablating RF electrodes may also be utilized. In various embodiments, multiple flexible electrode segments may be separated by less flexible, and non-conductive, intermediate segments, as disclosed in U.S. Patent publication 2013/0085479.

In various embodiments of the present disclosure, the flexible electrode coils may take various shapes, orientations, and patterns about the balloon. For example, circular, elliptical, "D" shape, among other shapes that may facilitate improved electrode-tissue contact. Some embodiments may include a plurality of flexible electrode coils that form multiple loops, and when activated create multiple contiguous transmural circumferential lesions. This type of redundant electrode coil configuration may greatly reduce the probability of incomplete electrical signal blockage across the multiple lesions. In many embodiments, an external structure may support the electrode coils, as well as irrigant lumens and ports, and mapping electrodes interspersed between the RF electrodes.

Various embodiments may include ring electrodes at proximal and distal ends of the ablation balloon to facilitate localization of the ablation balloon catheter within a patient (e.g., magnetic and impedance-based 3-D mapping). A junction between the catheter shaft and the balloon may also include a contact force sensor for determining a contact force between the electrode coils and tissue during an ablation therapy.

While the various figures of the present disclosure are generally directed toward RF ablation techniques, such embodiments may be readily adapted to facilitate various known ablation technologies including ultrasound, cryoablation, among others. In cryoablation implementations, an external structure surrounding the balloon may include cryofluid supply lumen(s) that deliver a cryogenic fluid from a cryofluid supply at a distal end of a catheter shaft to one or more expansion chambers about the balloon. When the balloon is inflated, each of the expansion chambers within the external structure are placed into substantially equal contact with the PV tissue surrounding the balloon. Accordingly, upon introduction of cryofluid to the expansion chambers, the rapid expansion of the cryogenic fluid into a gas phase absorbs a large amount of energy—thereby drawing energy out of the contacting tissue to achieve ablation.

In one specific balloon catheter embodiment for cryogenic ablation, an external structure, surrounding a balloon, may include one or more lumens that deliver cryogenic fluid to one or more expansion chambers distributed along a length of the external structure. This embodiment is readily adaptable for two or more external structures surrounding all or a portion of a balloon. Cryogenic fluid is delivered, via the one or more lumens within the one or more external structures, to the one or more expansion chambers—which induces cooling of electrodes in proximity to the cooling chamber. Where the electrodes are in contact with tissue, the tissue will be ablated resulting in lesioned tissue. In more specific embodiments, temperature sensors may be placed on or near the electrodes to monitor the cooling of the electrodes and also to facilitate control system feedback loops which may increase or decrease cryogenic fluid flow through the lumens and into the one or more cooling chambers based on a desired ablation temperature.

Embodiments of the present disclosure may utilize irrigant fluid to inflate a balloon and thereby extend RF electrodes on an electrode coil into contact with PV tissue. In such embodiments, the balloon may include irrigant ports that facilitate irrigation in proximity to the electrode coil(s). Various irrigant ports (also referred to as weeping holes) are disclosed in U.S. Pat. No. 6,251,109, which is hereby incorporated by reference as though fully set forth herein. Moreover, the balloon profile may include one or more concave features to facilitate positioning of the electrode coils about the balloon while limiting the longitudinal motion of the electrode coils relative to the balloon. The irrigant ports facilitate fluid flow about the interface between the electrode coil and the balloon to limit blood charring on the electrode coil and blood coagulation.

External structures that contain RF electrodes (or the electrode coils themselves) may take a variety of cross-sectional shapes including round, elliptical, half-circular, and rectangular, for example.

Various embodiments of the electrode coils are directed to single-loop designs where a first external support structure extends over the balloon from a proximal end of the balloon to a position on the balloon where a target tissue will contact the balloon once the ablation catheter is delivered. A single-loop electrode coil circumferentially extends from the distal end of the first external support structure around the balloon and is coupled to a second external support structure that extends longitudinally to a distal end of the ablation balloon. In yet other embodiments, the second external support structure may instead extend back to a proximal end of the balloon. The external support structure may be a hollow tube to facilitate lead wires necessary to operate the RF coils, diagnostic electrodes, mapping electrodes, etc. In yet other embodiments, the lead wires may be run external to the external support structures.

Some embodiments of electrode coils disclosed herein are directed to double-loop designs. In such embodiments, two external support structures extend distally from a proximal end of the balloon interface with the catheter shaft to a position on the balloon where a target tissue will contact the balloon. Electrode coils coupled to each of the external support structures circumferentially extend around the balloon in opposite directions. Each of the electrode coils extend approximately 180 degrees around the circumference of the balloon, where the electrode coils are coupled to another set of external support structures that extend to a distal end of the ablation balloon. In yet other embodiments, the other set of external support structures may instead extend back to a proximal end of the balloon. It may further be advantageous to combine or otherwise couple the paired external support structure to improve structural rigidity.

Aspects of the present disclosure are directed to an ablation balloon which utilizes direct current applied across target pulmonary vein tissue to cause ablation (also referred to as irreversible electroporation). In such embodiments, the electrode coil includes irreversible electroporation (IRE) electrodes distributed about a circumference of the balloon (similar to the RF embodiments disclosed above). An electroporation pulse generated by a source may transmit an IRE pulse through lead wires extending a length of the catheter shaft to the IRE electrodes which are in contact with tissue—thereby ablating the tissue.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation balloon catheter apparatus comprising:
a catheter shaft including proximal and distal ends;

a balloon including proximal and distal ends, the proximal end of the balloon coupled to a distal end of the catheter shaft; and an electrode coil configured to transfer energy between the electrode coil and tissue in contact with the electrode coil, wherein the electrode coil includes a first portion and a second portion, the first portion of the electrode coil extends circumferentially around a first half of the balloon, and the second portion of the electrode coil extends circumferentially around a second half of the balloon.

2. The apparatus of claim 1, wherein the balloon is configured to engage a pulmonary vein of a cardiac muscle along a length and circumference of the balloon, thereby placing the electrode coil into contact with a circumferential portion of the pulmonary vein, and the electrode coil is further configured to deliver a tissue ablation therapy to the circumferential portion of the pulmonary vein in contact with the electrode coil.

3. The apparatus of claim 2, wherein the balloon is further configured to insulate the pulmonary vein tissue engaged by the balloon from the tissue ablation therapy, the first portion of the electrode coil wraps around the balloon in a first direction, and the second portion of the electrode coil wraps around the balloon in a second direction opposite the first direction.

4. The apparatus of claim 1, wherein the electrode coil is positioned at a central portion of the balloon relative to a longitudinal axis of the apparatus, and the electrode coil is further configured to deliver a tissue ablation therapy along a circumference of a pulmonary vein ostium in contact with the electrode coil.

5. The apparatus of claim 1, wherein the electrode coil is situated at a distal end of the balloon relative to a longitudinal axis of the apparatus, and the electrode coil is configured and arranged to deliver a tissue ablation therapy along a circumference of a pulmonary vein antrum in contact with the electrode coil.

6. The apparatus of claim 1, further including
a signal generator configured to generate a signal; and
wherein the electrode coil includes a plurality of radio frequency electrodes, the radio frequency electrodes electrically coupled to the signal generator, and the radio frequency electrodes are configured to
engage a first length and circumference of a pulmonary vein, and
emit radio frequency waves, in response to the generated signal, that ablates the pulmonary vein tissue in contact with the radio frequency electrodes.

7. The apparatus of claim 6, wherein the balloon is configured to
engage a second length and circumference of the pulmonary vein adjacent to the first length and circumference of the pulmonary vein, and
shield the pulmonary vein tissue in contact with the balloon from the radio frequency waves transmitted by the radio frequency electrodes.

8. The apparatus of claim 1, wherein each of the first and second portions of the electrode coil is coupled to the catheter shaft distal the balloon, and proximal the balloon.

9. The apparatus of claim 1, wherein the electrode coil includes one or more of the following: diagnostic electrodes, thermocouples, and magnetic or impedance-based mapping sensors.

10. The apparatus of claim 1, wherein the electrode coil includes diagnostic electrodes configured to detect electrophysiological characteristics of tissue in contact with the diagnostic electrodes.

11. The apparatus of claim 1, wherein energy is transferred between the electrode coil and tissue in contact with the electrode coil via irreversible electroporation.

12. The apparatus of claim 1, wherein the electrode coil is configured to receive a cryogenic fluid that absorbs heat from tissue in contact with the electrode coil, and
the balloon is further configured to insulate the cryogenic fluid from heat associated with a blood pool and tissue in contact with the balloon.

13. A system for treating atrial fibrillation, the system comprising:
an introducer including a lumen extending through a length of the introducer;
a balloon delivery catheter configured to extend through the lumen of the introducer;
a balloon coupled to a distal end of the balloon delivery catheter; and
an electrode coil configured to
engage with a tissue wall of a pulmonary vein, and
deliver an ablation therapy along the tissue wall of the pulmonary vein engaged by the electrode coil;
wherein the electrode coil includes a first portion and a second portion, the first portion of the electrode coil extends circumferentially around a first half of the balloon in a first direction, and the second portion of the electrode coil extends circumferentially around a second half of the balloon in a second direction opposite the first direction.

14. The system of claim 13, wherein the balloon is configured to
engage with a length and circumference of the pulmonary vein adjacent to the tissue wall engaged with the electrode coil, and
insulate the length and circumference of the pulmonary vein engaged by the balloon from the ablation therapy.

15. The system of claim 13, further including a signal generator, and wherein the electrode coil includes a plurality of radio frequency coils, the plurality of radio frequency coils electrically coupled to the signal generator via lead wires extending through a length of the balloon delivery catheter, and configured to receive a generated signal from the signal generator and emit a radio frequency signal.

16. The system of claim 13, wherein the electrode coil is further configured to receive a cryofluid that absorbs heat from the tissue wall of the pulmonary vein engaged with the electrode coil; and
the balloon is configured to insulate the cryofluid from heat within the tissue wall of the pulmonary vein in contact with the balloon.

17. A balloon catheter for pulmonary vein isolation comprising:
a steerable balloon delivery catheter shaft configured to deploy a balloon into a pulmonary vein;
the balloon is coupled to a distal end of the steerable balloon delivery catheter shaft, and configured to
deploy from an undeployed configuration, and
engage a tissue wall of the pulmonary vein; and
a tissue ablation means including first and second portions coupled to the distal end of the catheter shaft and extending distally together along a surface of the balloon, wherein at a mid-point of the balloon, the first portion extends circumferentially about the balloon in a first direction and the second portion extends circumferentially about the balloon in a second direction opposite the first direction, and wherein the first and second portions meet at the opposite side of the balloon and extend distally together along a surface of the balloon and are coupled to the distal end of the balloon; wherein the tissue ablation means is configured to deliver an ablation therapy to the tissue wall of the pulmonary vein in contact with the tissue ablation means.

18. The balloon catheter of claim 17, wherein the tissue ablation means is one or more of the following: cryoablation, irreversible electroporation, laser energy, radio frequency energy, microwave energy, chemical reaction, and high-intensity focused ultrasound.

19. The balloon catheter of claim 17, wherein the tissue ablation means is positioned near a distal portion of the balloon, and is further configured to engage and to conduct an ablation therapy of an antral circumference of the pulmonary vein, the proximal portion of the balloon configured and arranged to insulate a blood pool and the pulmonary vein tissue in contact with a proximal portion of the balloon.

20. The balloon catheter of claim 17, wherein the balloon is configured to mitigate the delivery of the ablation therapy to the tissue wall of the pulmonary vein in contact with the balloon.

\* \* \* \* \*